United States Patent
Isab et al.

(10) Patent No.: US 9,572,822 B2
(45) Date of Patent: *Feb. 21, 2017

(54) TREATMENT OF CERVICAL CANCER WITH GOLD(I) COMPLEXES

(71) Applicants: KING FAHD UNIVERSITY OF PETROLEUM AND MINERALS, Dhahran (SA); KING ABDULAZIZ CITY FOR SCIENCE AND TECHNOLOGY, Riyadh (SA)

(72) Inventors: Anvarhusein Abdulkadir Isab, Dhahran (SA); Muhammad Altaf, Dhahran (SA); Muhammad Monim-Ul-Mehboob, Dhahran (SA); Adam Ahmed Abdallah Seliman, Dhahran (SA); Mohammed Ismail Wazeer, Dhahran (SA)

(73) Assignees: King Fahd University of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/282,716

(22) Filed: Sep. 30, 2016

(65) Prior Publication Data

US 2017/0020901 A1    Jan. 26, 2017

Related U.S. Application Data

(60) Continuation of application No. 15/042,852, filed on Feb. 12, 2016, now Pat. No. 9,492,465, which is a division of application No. 14/219,794, filed on Mar. 19, 2014, now abandoned.

(51) Int. Cl.
*A61K 31/66* (2006.01)
*C07F 9/50* (2006.01)
*G01N 33/50* (2006.01)

(52) U.S. Cl.
CPC ............ *A61K 31/66* (2013.01); *C07F 9/5045* (2013.01); *G01N 33/5011* (2013.01); *G01N 33/5044* (2013.01)

(58) Field of Classification Search
CPC ... A61K 31/66; C07F 9/5045; G01N 33/5011; G01N 33/5044
See application file for complete search history.

(56) References Cited

U.S. PATENT DOCUMENTS

| | | | |
|---|---|---|---|
| 6,548,540 B2 | 4/2003 | Kennedy | |
| 6,706,759 B1 | 3/2004 | Kennedy | |
| 8,481,496 B2 | 7/2013 | Fregona et al. | |
| 2007/0232692 A1 | 10/2007 | Kennedy | |
| 2009/0076267 A1* | 3/2009 | Kodama | C07F 1/005 544/225 |

FOREIGN PATENT DOCUMENTS

EP    2161045 A2    3/2010

OTHER PUBLICATIONS

Gandin, V., et al., "Cancer Cell Death Induced by Phosphine Gold (I) Compounds Targeting Thioredoxin Reductase", Biochemical Pharmacology, vol. 79, pp. 90-101 (2010).
Meislich, H., et al., "Schaum's Outline of Theory and Problems of Organic Chemistry", McGraw-Hill, $3^{rd}$ Edition, 3 Pages total, (1999).
Scheffler et. al., Polyhedron, 2010, Elsevier, vol. 29, pp. 66-69.
Chabner et. al., Nature Reviews Cancer, 2005, Nature Publishing Group, vol. 5, pp. 65-72.
Leaf, Fortune, Mar. 2004, Time Inc., pp. 1-28.

* cited by examiner

*Primary Examiner* — Sarah Pihonak
(74) *Attorney, Agent, or Firm* — Oblon, McClelland, Maier & Neustadt, L.L.P.

(57) ABSTRACT

Gold(I) complexes of formulae $[Au\{P(t-Bu)_3\}(S_2CN(CH_3)_2)]$ (1), and $[Au\{P(t-Bu)_3\}(S_2CN(C_2H_5)_2)]$ (2) have been prepared by the reaction of equimolar amounts of $[Au\{P(t-Bu)_3\}(Cl)]$ with sodium dimethyldithiocarbamate monohydrate, and sodium diethyldithiocarbamate trihydrate respectively. Both complexes (1) and (2) are iso-structural having linear geometry. These gold(I) dithiocarbamate complexes show in vitro cytotoxic activities against A549 (human lung carcinoma), HeLa (human cervical cancer) and MCF7 (human breast cancer) cell lines.

2 Claims, 5 Drawing Sheets

TREATMENT OF CERVICAL CANCER WITH GOLD(I) COMPLEXES

CROSS-REFERENCE TO RELATED APPLICATIONS

The present application is a continuation of Ser. No. 15/042,852, now allowed, which is a Divisional application of U.S. application Ser. No. 14/219,794, now abandoned, filed on Mar. 19, 2014. The entire contents of which are incorporated herein by reference.

BACKGROUND OF THE INVENTION

Technical Field

The present disclosure relates to two linear gold(I) dithiocarbamate complexes containing a $R_2N$—$CS_2$ thioureide bond, a method of making the linear gold(I) dithiocarbamate complexes, and a method of the cytotoxic treatment of cancer cells.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Transition metal complexes of common ligands with group 15 (Nitrogen, Phosphorus and Arsenic) and group 16 (Oxygen, Sulfur, Selenium) donor atoms have been extensively investigated in various fields of bioinorganic chemistry, electrochemistry and organometallic chemistry. The study of gold complexes bearing different functional ligands exhibiting interesting physical, chemical, biological and pharmacological properties, has gained much attention (K. Nomiya, R. S. Yamamoto, R. Noghuchi, H. Yokoyama, N. C. Kasuga, K. Ohyama, C. Kato, J. Inorg. Biochem. 95 (2003) 208-220; T. McCormick, W. L. Jia, S. Wang, Inorg. Chem. 45 (2006) 147-155; S. S. Al-Jaroudi, M. I. M. Wazeer, A. A. Isab, S. Altuwaijri, Polyhedron. (2013) 434-442; R. B. Bostancioglu, K. Isik, H. Genc, K. Benkli, A. T. Koparal, Medicinal Chemistry. 27 (2012) 458-466—each incorporated herein by reference in its entirety).

There was substantial interest in the coordination chemistry of Au(I) complexes showing biological activity with potential medicinal applications. For instance, currently used drugs like Auranofin, Solganol and Myocrisin are Au(I)—S complexes (S. H. van Rijt, P. J. Sadler, Drug Discovery Today, 14 (2009) 1089-1097; R. Noghuchi, A. Hara, A. Sugie, K. Nomiya, Inorg. Chem. Commun. 9 (2006) 355-359; K. Nomiya, R. Noghuchi, K. Ohsawa, K. Tsuda, M. Oda, J. Inorg. Biochem. 78 (2000) 363-370; B. P. Howe, Metal Based Drugs. 4 (1997) 273-277; V. J. Ctalano, A. O. Etogo, J. Organomet. Chem. 690 (2005) 6041-6050—each incorporated herein by reference in its entirety). Consequently, gold(I) complexes have long been studied as anti-arthritic and anti-microbial agents (O. Crespo, V. V. Brusko, M. C. Giameno, M. L. Tornil, A. Laguna, N. G. Zabirov, Eur. J. Inorg. Chem. 2 (2004) 423-430; K. Nomiya, R. Noghuchi, M. Oda, Inorg. Chim. Acta. 298 (2000) 24-32; H. Q. Liu, T.-C. Cheung, S.-M. Peng, C.-M. Che, J. Chem. Soc., Chem. Commun. (1995) 1787-1788; C. J. O'Connor, E. Sinn, Inorg. Chem. 17 (1978) 2067-2071; M. A. Cinellu, G. Minghetti, M. V. Pinna, S. Stoccoro, A. Zucca, M. Manassero, M. Sansoni, J. Chem. Soc., Dalton Trans., (1998) 1735-1742—each incorporated herein by reference in its entirety). It has been found that gold(I)-phosphine complexes with P—Au—P, P—Au—N, P—Au—S, and S—Au—S bonding show marked biological activities against bacteria and yeast (K. Nomiya, S. Takahashi, R. Noghuchi, J. Chem. Soc., Dalton Trans. (2000) 2091-2097; R. C. Elder, K. Ludwig, J. N. Cooper, M. K. Eidsness, J. Am. Chem. Soc. 107 (1985) 5024-5025—each incorporated herein by reference in its entirety). Gold(I) phosphine complexes are known to exhibit promising anticancer properties (R. W.-Y. Sun, C.-M. Che, Coord. Chem. Rev., 253 (2009) 1682-1691; P. Papathanasiou, G. Salem, P. Waring, A. C. Willis. J. Chem. Soc., J. Chem. Soc. Dalton Trans., (1997) 3435-3443; H. Lv, B. Yang, J. Jing, Y. Yu, J. Zhang, J.-L. Zhang, Dalton Trans., 41 (2012) 3116-3118—each incorporated herein by reference in its entirety). In this connection, Lorber et al in 1979, firstly reported that Auranofin could inhibit the in vitro proliferation of HeLa cells (T. M. Simon, D. H. Kunishima, G. J. Vibert, A. Lorber, Cancer, 44 (1979) 1965-1975—incorporated herein by reference in its entirety). Berners-Price and coworkers reported Bis(diphosphino)gold(I) compounds and demonstrated promising in vivo anti-cancer activities (S. J. Berners-Price, C. K. Mirabelli, R. K. Johnson, M. R. Mattern, F. L. Mccabe, L. F. Faucette, C. M. Sung, S. M. Mong, P. J. Sadler, S. T. Crooke, Cancer Res. 46 (1986) 5486—incorporated herein by reference in its entirety). Again Berners-Price et al pointed out $[Au(dppe)_2]^+$ and its derivatives as their persuasive in vitro and in vivo anti-cancer activities via the mitochondrial-mediated apoptotic pathway (M. J. McKeage, L. Maharaj, S. J. Berners-Price, Coord. Chem. Rev. 232 (2002) 127-135—incorporated herein by reference in its entirety). Barnard et al recently recognized a series of gold(I) compounds with carbene ligands (P. J. Barnard, S. J. Berners-Price, Coord. Chem. Rev. 251 (2007) 1889-1902—incorporated herein by reference in its entirety).

In the first decade of the 21st century, a new class of gold complexes with dithiocarbamate ligands has emerged as anticancer agents. In this regard, Fregona and coworkers firstly prepared and characterized gold(III) dithiocarbamate compounds containing N,N-dimethyldithiocarbamate and ethylsarcosinedithiocarbamate showing a very promising chemical and biological profile (L. Ronconi, L. Giovagnini, C. Marzano, F. Bettio, R. Graziani, G. Pilloni, D. Fregona, Inorg. Chem. 44 (2005) 1867-1881—incorporated herein by reference in its entirety) Treatment with dibromo(N,N-dimethyldilhiocarbamato)gold(III) resulted in significant inhibition of in-vivo MDA-MB-231 breast tumor growth (V. Milacic, D. Chen, L. Ronconi, K. R. Landis-Piwowar, D. Fregona, Q. P. Dou, Cancer Res. 66 (2006) 10478-10486—incorporated herein by reference in its entirety). Zhang et al reported that gold(I)-dithiocarbamato species, namely [Au (ESDT)](2) could inhibit the chymotrypsin-like activity of purified 20S proteasome and 26S proteasome in human breast cancer MDA-MB-231 cells, resulting in accumulation of ubiquitinated proteins and proteasome target proteins, and induction of cell death (X. Zhang, M. Frezza, V. Milacic, L. Ronconi, Y. Fan, C. Bi, D. Fregona, Q. P. Dou, J. Cell Biochem. 109(1) (2010) 162-72—incorporated herein by reference in its entirety).

In recent years, research has increasingly focused on the potential of gold complexes as anticancer drug candidates (S. Ahmad, A. A. Isab, S. Ali, A. R. Al-Arfaj, Polyhedron. 25 (2006) 1633-1645; D. V. Partyka, T. J. Robilotto, M. Zeller, A. D. Hunter and T. G. Gray, Proc. Natl. Acad. Sci. U.S.A 105 (2008) 14293-14297; Y. Wang, Q.-Y. He, C.-M. Che, J.-F. Chiu, Proteomics. 6 (2006) 131-142; Y. Shi, W. Chu, Y. Wang, S. Wang, J. Du, J. Zhang, S. Li, G. Zhou, X. Qin, C.

Zhang, Inorg. Chem. Commun. 30 (2013) 178-181; M. Monim-ul-Mehboob, M. Altaf, M. Fettouhi, A. A. Isab, M. I. M. Wazeer, M. N. Shaikh, S. Altuwaijri, Polyhedron. 61 (2013) 225-234—each incorporated herein by reference in its entirety). Gold(I) thiolates employed clinically in the treatment of rheumatoid arthritis display some potency against various tumors but a greater potential is found in their analogues. In particular, analogues featuring a linear P—Au—S arrangement in which the thiolate ligand is derived from a biologically active thiol display high potency (E. R. Tiekink, Crit. Rev. Oncol. Hematol. 42 (2002) 225-48—incorporated herein by reference in its entirety).

The synthesis of gold(I) complexes of phosphine with dialkyl dithiocarbamate mixed ligands, their structure analysis by IR spectroscopy and NMR measurements, and their structure determination by single crystal X-ray crystallography is disclosed herein. Finally, well characterized gold (I) complexes have systematically been evaluated for in vitro cytotoxic activity against various human cancer cell lines e.g. A549 (human lung carcinoma), MCF7 (human breast cancer), and HeLa (human cervical cancer) cell lines.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One embodiment of the disclosure relates to a linear gold complex.

In another embodiment, the linear gold complex is [Au{P(t-Bu)$_3$}(S$_2$CN(CH$_3$)$_2$].

In another embodiment, the linear gold complex is [Au{P(t-Bu)$_3$}(S$_2$CN(C$_2$H$_5$)$_2$)].

In another embodiment, a method is disclosed for measuring the cytotoxicity of the linear gold complex.

In another embodiment, the method includes incubating a cancer cell, contacting the cancer cell with any of the linear gold complexes, and absorbing the wells to measure cell death.

In another embodiment, the method includes administering one or more of the gold complexes in a cytotoxically effective amount sufficient to treat a patient in need of treatment for cancer.

In another embodiment the method is used to treat cancer from the HeLa cell line.

In another embodiment the method is used to treat cancer from the A549 cell line.

In another embodiment the method is used to treat cancer from the MCF7 cell line.

In another embodiment, the linear gold complex [Au{P(t-Bu)$_3$}(S$_2$CN(CH$_3$)$_2$] is used to treat cancer from the HeLa cell line.

In another embodiment, the HeLa cell line can be treated with the gold complexes having an IC$_{50}$ concentration in the range of 2.070-3.212 µM.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
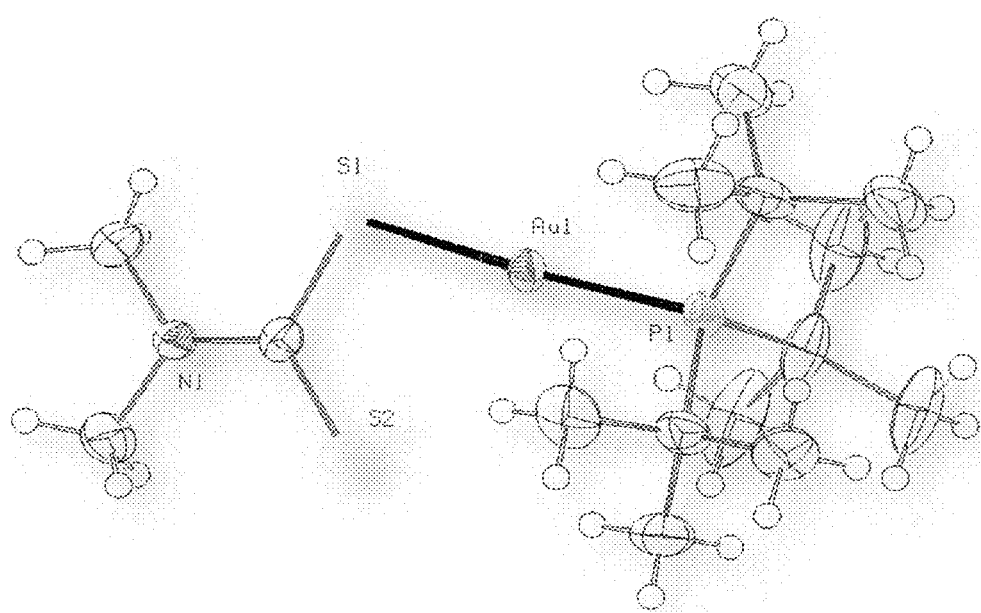
FIG. 1 illustrates the molecular structure of mononuclear complex 1.

Referring now to the drawings, wherein like reference numerals designate identical or corresponding parts throughout the several views.

Two new linear gold(I) complexes of formulae [Au{P(t-Bu)$_3$}(S$_2$CN(CH$_3$)$_2$)] (1), and [Au{P(t-Bu)$_3$}(S$_2$CN(C$_2$H$_5$)$_2$)] (2) have been prepared by the reaction of equimolar amounts of [Au{P(t-Bu)$_3$}(Cl)] with sodium dimethyldithiocarbamate monohydrate, and sodium diethyldithiocarbamate trihydrate respectively. The structures of the complexes (1) and (2) have been determined by single X-ray crystallography. Both complexes (1) and (2) are iso-structural having linear geometry. The coordination geometry around Au(I) cation is analogous in many aspects. The complex (1) crystallizes in monoclinic space group 'P 2$_1$/a', while the complex (2) crystallizes in orthorhombic space group 'P 2$_1$2$_1$2$_1$'. IR spectroscopy confirms the presence of thioureide bond (R$_2$N—CS$_2$) in the complexes (1) and (2). The $^1$H, $^{13}$C and $^{31}$P NMR, and IR spectra of the Au(I) complexes (1) and (2) corroborate with their single crystal X-ray structure analyses. These gold(I) dithiocarbamate complexes show selective and promising in vitro cytotoxic activities against A549 (human lung carcinoma), HeLa (human cervical cancer) and MCF7 (human breast cancer) cell lines. Complex (0), Complex (1), and Complex (2) are presented below:

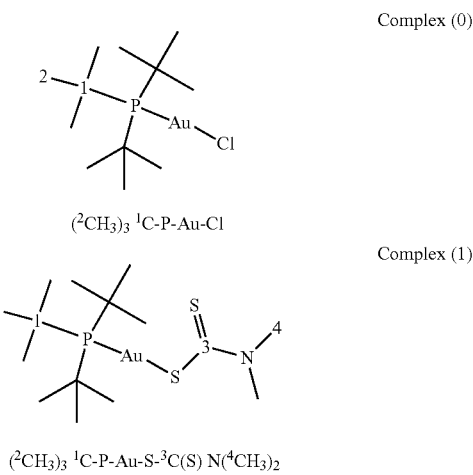

Complex (0)

($^2$CH$_3$)$_3$ $^1$C-P-Au-Cl

Complex (1)

($^2$CH$_3$)$_3$ $^1$C-P-Au-S-$^3$C(S) N($^4$CH$_3$)$_2$

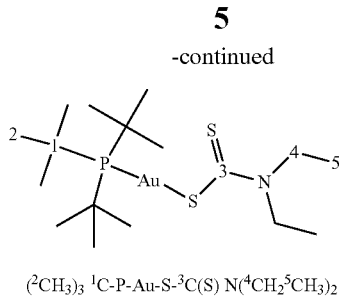

Complex (2)

($^2$CH$_3$)$_3$ $^1$C-P-Au-S-$^3$C(S) N($^4$CH$_2$$^5$CH$_3$)$_2$

The formation of the gold complex (1) includes a mixing a gold complex with a halogen precursor compound with a solvent and a salt to induce a salt-elimination reaction. The resulting compound is then filtered and crystallized via slow evaporation for the formation of crystals which forms the gold complex [Au{P(t-Bu)$_3$}(S$_2$CN(CH$_3$)$_2$].

The formation of the gold complex (2) includes a mixing a gold complex with a halogen precursor compound with a solvent and a salt to induce a salt-elimination reaction. The resulting compound is then filtered and crystallized via slow evaporation for the formation of crystals which forms the gold complex [Au{P(t-Bu)$_3$}(S$_2$CN(C$_2$H$_5$)$_2$)].

Dialkyl dithiocarbamate complexes may stabilize a variety of oxidation states and coordination geometries, and seemingly small modifications to the ligand can lead to significant changes in the structure-behavior of the complexes formed. The structural parameters of the dithiocarbamate ligands are not modified significantly on coordination to gold(I) center.

Gold complexes are well known for their broad spectrum therapeutic and cytotoxic activity against bacterial pathogens, together with their lack of cross-resistance with antibiotics. The X-ray structures of both complexes with PAuS moiety have near linear geometry, which is typical for gold(I) complexes with group 15 donor atoms ligands.

EXAMPLES

All the reactions were carried under normal ambient conditions. All chemical and solvents used in the synthesis were of analytical grade and were used without further purification. All chemicals were purchased from Sigma-Aldrich St. Louis, Mo. United States and Strem Chemicals, Massachusetts, United States. Elemental analyses were performed on Perkin Elmer Series 11 (CHNS/O), Analyzer 2400.

The solid state FTIR spectra of the ligands and their gold(III) complexes were recorded on a Perking Elmer FTIR 180 spectrophotometer or NICOLET 6700 FTIR using KBr pellets over the range 4000-400 cm$^{-1}$ and Far-IR spectra were recorded for complexes at 4 cm$^{-1}$ resolution at room temperature as Cesium Chloride disks on a Nicolet 6700 FT-IR with Far-IR beam splitter. $^1$H, and $^{13}$C, and $^{31}$P NMR spectra were recorded on a LAMBDA 500 spectrophotometer operating at 500.01, 125.65 and 200.0 MHz respectively, corresponding to a magnetic field of 11.74 T. Tetramethylsilane (TMS) was used as an internal standard for $^1$H and $^{13}$C, while Triphenylphosphine (TPP) was used as an external standard for $^{31}$P. The $^{13}$C NMR spectra were obtained with $^1$H broadband decoupling, and the spectral conditions were: 32 k data points, 0.967 s acquisition time, 1.00 s pulse delay and 45° pulse angle. The $^1$H, $^{13}$C and $^{31}$P NMR chemical shifts are given in Tables 1-3, respectively. Table 1, Table 2, and Table 3 are presented below.

TABLE 1

IR frequencies (cm$^{-1}$) of complexes (0), (1) and (2)

| Free ligand/ complex | Stretch C—H(CH$_3$) | Bend C—H(CH$_3$) | Stretch C—H(CH$_2$) | Bend C—H(CH$_2$) | Stretch C=S | Stretch S=C—N |
|---|---|---|---|---|---|---|
| Free dimethyl-dithiocarbamte | 2924 | 1360 | — | — | 962 | 1488 |
| (1) | 2962(asym), 2869 (sym) | 1372 | — | — | 1022, 972 | 1479 |
| Free dimethyl-dithiocarbamte | 2925 | 1358 | 2979 | 1379 | 986 | 1466 |
| (2) | 2965(asym), 2867(sym) | 1371 | 2925 | 1409 | 1020, 989 | 1478 |

TABLE 2

Far IR frequencies (cm$^{-1}$) of complexes (0), (1) and (2)

| Complex | Au—Cl (cm$^{-1}$) | Au—P (cm$^{-1}$) | Au—S (cm$^{-1}$) |
|---|---|---|---|
| (0) | 304.1 | 194.3 | — |
| (1) | — | 194.3 | 281.6 |
| (2) | — | 194.3 | 281.6 |

TABLE 3

Solution $^1$H NMR chemical shifts (ppm) of the free gold(I) metal precursor and complexes 1 and 2.

| Specie | 2-H | 4-H | 5-H |
|---|---|---|---|
| [Au(P(t-Bu)$_3$)(Cl)] | 1.52 | — | — |
| Free NaS$_2$CN(CH$_3$)$_2$ · H$_2$O | — | 3.55 | — |
| [Au(P(t-Bu)$_3$)(S$_2$CN(CH$_3$)$_2$)] | 1.55 | 3.48 | — |
| Free NaS$_2$CN(C$_2$H$_5$)$_2$ · 3H$_2$O | — | 1.23 | 4.03 |
| [Au(P(t-Bu)$_3$)(S$_2$CN(C$_2$H$_5$)$_2$)] | 1.41 | 1.21 | 3.92 |

[Au{P(t-Bu)$_3$}(Cl)] (0.217 g, 0.05 mmol) in 10 mL Dichloromethane was added Sodium dimethyldithiocarbamate monohydrate (0.072 g, 0.05 mmol) in 15 mL Ethanol at room temperature with continuous stirring for 3 h. The clear light yellow solution obtained was filtered to avoid any impurity and kept undisturbed for crystallization by slow evaporation at room temperature. After seven days colorless block like crystals were obtained. A suitable quality crystal was chosen for X-ray diffraction analysis. Anal. Calc. for C$_{15}$H$_{33}$AuNPS$_2$: C, 34.68; H, 6.40; N, 2.70; S, 12.34. Found: C, 34.80; H, 6.33; N, 2.82; S, 12.43. Yield: 0.242 g, (93%).

[Au(P(t-Bu)$_3$)(Cl)] (0.217 g, 0.05 mmol) in 10 mL Dichloromethane was added Sodium diethyldithiocarbamate trihydrate (0.113 g, 0.05 mmol) in 15 mL of Ethanol at room temperature with continuous stirring for 3 h. The transparent yellow solution obtained was filtered to avoid any impurity and kept undisturbed for slow evaporation at room temperature. After five days colorless block like crystals were obtained. A suitable quality crystal was chosen for X-ray diffraction analysis. Anal. Calc. for $C_{17}H_{37}AuNPS_2$: C, 37.29; H, 6.81; N, 2.56; S, 11.71. Found: C, 37.19; H, 6.37; N, 2.70; S, 11.68. Yield: 0.260 g, (95%).

For gold(I) complexes (1) and (2), quality single X-ray crystal, which was obtained from $C_2H_5OH$ solution, was mounted on a plastic loop to an Agilent Super Nova diffractometer equipped with a Mo Ka radiation (1=0.71073 Å). The data were collected and integrated with CrysAlis-PRO (Agilent (2011). Crys Alis PRO. Agilent Technologies, Yarnton, England—incorporated herein by reference in its entirety). The structure was solved with direct method and refined by least square method with Olex2 (O. V. Dolomanov, L. J. Bourhis, R. J. Gildea, J. A. K. Howard, H. Puschmann, J. Appl. Cryst. 42 (2009) 229-341—incorporated herein by reference in its entirety). Graphics were generated using PLATON and MERCURY (C. F. Macrae, P. R. Edgington, P. McCabe, E. Pidcock, G. P. Shields, R. Taylor, M. Towler, J. van de Streek, J. Appl. Cryst. 39 (2006) 453-457—incorporated herein by reference in its entirety). A summary of crystal data and refinement details for gold(I) complexes (1) and (2) are given in Table 4. Table 4 is presented below.

TABLE 4

Solution $^{13}C$ and $^{31}P$ NMR chemical shifts (ppm) of the free gold(I) metal precursor and Au(I) complexes 1 and 2.

| Complex | C=S | C-1 ($J_{PC}$ in Hz) | C-2 | C-4 | C-5 | $^{31}P$ |
|---|---|---|---|---|---|---|
| [Au(P(t-Bu)$_3$)(Cl)] | — | 39.42(20.6) | 32.23 | — | — | 200.02 |
| Free NaS$_2$CN (CH$_3$)$_2$•H$_2$O | 212.82 | — | — | 45.12 | — | — |
| [Au(P(t-Bu)$_3$) (S$_2$CN(CH$_3$)$_2$)] | 207.49 | 39.31(17.5) | 32.21 | 45.16 | — | 207.49 |
| Free NaS$_2$CN (C$_2$H$_5$)$_2$•3H$_2$O | 206.70 | — | — | 49.61 | 12.31 | — |
| [Au(P(t-Bu)$_3$) (S$_2$CN(C$_2$H$_5$)$_2$)] | 205.87 | 39.25(17.5) | 32.18 | 48.94 | 12.14 | 205.87 |

Selected bond lengths and bond angles are given in Table 5. Table 5 is presented below.

TABLE 5

Crystallographic characteristics, experimental and structure refinement details for crystal structure of complex complexes 1 and 2

| | Complex 1 | Complex 2 |
|---|---|---|
| Empirical formula | C$_{15}$H$_{33}$AuNPS$_2$ | C$_{17}$H$_{37}$AuNPS$_2$ |
| Empirical formula weight | 519.48 | 547.53 |
| Crystal size/mm | 0.2 × 0.2 × 0.05 | 0.1 × 0.1 × 0.1 |
| Wavelength/Å | 0.71073 | 0.71073 |
| Temperature/K | 200 (2) | 200 (2) |
| Crystal symmetry | Monoclinic | Orthorhombic |
| Space group | P2$_1$/a | P2$_1$2$_1$2$_1$ |
| a/Å | 11.6216 (7) | 13.6063 (8) |
| b/Å | 12.5419 (6) | 13.6398 (9) |
| c/Å | 14.3661 (9) | 23.7965 (13) |
| α/° | 90 | 90 |
| β/° | 103.910 (6) | 90 |
| γ/° | 90 | 90 |
| V/Å$^3$ | 2032.5 (2) | 4416.3 (5) |
| Z | 4 | 8 |
| D$_c$/Mg m$^{-3}$ | 1.698 | 1.647 |
| μ(Mo-Kα)/mm$^{-1}$ | 7.52 | 6.92 |
| F(000) | 1024 | 2176 |
| θ Limits/° | 3.0-28.9 | 3.0-29.0 |
| Collected reflections | 10520 | 37465 |
| Unique reflections(R$_{int}$) | 3392 (0.043) | 9929 (0.043) |
| Observed eflections [F$_o$ > 2σ(F$_o$)] | 4775 | 10949 |
| Goodness of fit on F$^2$ | 1.04 | 1.05 |
| R$_1$(F),$^a$[I > 2σ (I)] | 0.037 | 0.035 |
| wR$_2$(F$^2$),$^b$[I > 2σ(I)] | 0.099 | 0.082 |
| Largest diff. peak, hole/e Å$^{-3}$ | 0.81, −1.88 | 3.26, −0.73 |

Metal precursor and two synthesized compound (1) and compound (2) were evaluated for their in-vitro cytotoxic activity against MCF7 (human breast cancer), HeLa (human cervical cancer) and A549 (human lung carcinoma) cell lines.

The cells were seeded at 4×10$^3$ cells/well in 100 μL DMEM (Dulbecco's Modified Eagle's Medium) containing 10%. FBS (Fetal Bovine Serum) in 96-wells tissue culture plate and incubated for 72 h at 37° C., 5% CO$_2$ in air and 90% relative humidity in CO$_2$ incubator. After incubation, 100 μL of complex (0), (1) and (2) (50, 25, 12.5, 6.25 and 3.12 μg/mL), prepared in DMEM, was added to cells and the cultures were incubated for 24 h. The medium of wells was discarded and 100 μL DMEM containing MTT (3-(4,5-Dimethylthiazol-2-Yl)-2,5-Diphenyltetrazolium Bromide) (5 mg/mL) was added to the wells and incubated in CO$_2$ incubator at 37° C. in dark for 4 h. After incubation, a purple colored formazan (artificial chromogenic dye, product of the reduction of water insoluble tetrazolium salts e.g., MMT by dehydrogenases and reductases) in the cells is produced and appeared as dark crystals in the bottom of the wells. The medium of culture was discarded from each well carefully to avoid disruption of monolayer and 100 μL of Dimethylsufoxide (DMSO) was added in each well. The solution was thoroughly mixed in the wells to dissolve the formazan crystals which ultimately result into a purple solution. The absorbance of the 96-wells plate was taken at 570 nm with Labsystems Multiskan EX-Enzyme-linked immunosorbent assay (EX-ELISA) reader against a reagent blank.

Dithiocarbamate compounds can be identified via the presence of certain absorbance peaks primarily v(C—N) and v(C—S). In the infrared spectra of dithiocarbamate compounds, the region 1480-1550 cm-1 is primarily associated with the R$_2$N—CSS 'thioureide' band which defines the carbon-nitrogen bond order between a single bond at 1250-1350 cm$^{-1}$ and a double bond at 1640-1690 cm$^{-1}$ (A. J. Odola, J. A. O. Woods, J. Chem. Pharm. Res., 3 (2011) 865-871—incorporated herein by reference in its entirety).

The most important band observed in IR spectra, known as thioureide band, v(C—N) was detected at 1479 cm$^{-1}$ and 1478 cm$^{-1}$ in complexes (1) and (2) respectively. Since these frequency modes lie in between those associated with single C—N and double C=N bonds hence the partial double bond character of thioureide bond was confirmed for both of the complexes (F. Jian, Z. Wang, Z. Bai, X. You, H. Fun, K. Chinnakali, L. A. Razak, Polyhedron, 18 (1999) 3401-3406—incorporated herein by reference in its entirety). The presence of the thioureide band between 1545-1430 cm$^{-1}$ suggest a considerable double bond character in the C . . . N bond vibration of the S$_2$C—NR$_2$ group (A. Jayaraju, M. M. Ahamad, R. M. Rao, J. Sreeramulu, Der Pharma Chemica, 4 (2012) 1191-1194.—incorporated herein by reference in its entirety). This strong absorption band (1542-1480 cm$^{-1}$) is known as the thioureide ion band. The band appears intermediate within C—N single bond (C—N: 1063-1261 cm$^{-1}$) and double bond (C=N: 1640-1690 cm$^{-1}$) wave numbers. This band shows the partial double bond feature that characterized the formation of dithiocarbamate (S$_2$C—NR$_2$). The stretching vibration from this partial double bond is due to the partial delocalization of electron density within the dithiocarbamate (H. Nabipour, S. Ghammamy, S. Ashuri, Z. S. Aghbolagh, J. Org. Chem., 2 (2010) 75-80—incorporated herein by reference in its entirety). A strong absorption in this region of the spectrum gives a good indication that the gold(I) complex has been satisfactorily prepared (J. Chatt, L. A. Duncanson, L. M. Venanzi, *Nature*, 177 (1956) 1042-1043—incorporated herein by reference in its entirety).

C=S thiocarbonyl stretch, splitting into two peaks (doublet) occur at 1022 cm$^{-1}$, 972 cm$^{-1}$ and 1020 cm$^{-1}$, 989 cm$^{-1}$ with medium intensity in complexes (1) and (2) respectively. The bands present in the range of 1022-972 cm$^{-1}$ is attributed to the prevailing contribution of (C . . . S). The presences of splitting to the v(C—S) bands that appeared in the range 965-972 cm$^{-1}$ indicates a monodentate nature of dialkyl dithiocarbamate ligands in the synthesized complexes (I. Raya, I. Baba, B. M. Yamin, Malaysia Journal of Analytical Sciences, 10 (2006) 93-98; W. Haas, T. Schwarz, Microchem. Ichonal. Acta, 58 (1963) 253-259; D. C. Onwudiwe, P. A. Ajibade, Polyhedron, 29 (2010) 1431-1436—each incorporated herein by reference in its entirety).

In addition to the polar thioureide ion band S$_2$C=N$^+$R$_2$, the usual bands for sp$^3$-hybridized carbon-hydrogen stretches are observed (3000-2840 cm$^{-1}$), which are very similar to those the sodium salt of diethyldithiocarbamate (C. J. Pouchert, *Aldrich Library of FT-IR Spectra*, 2nd ed.; Aldrich Chemical Company: Milwaukee, Vol. 1 (1997)—incorporated herein by reference in its entirety) In complexes (1) and (2), the stretch band frequency occurs below 3000 cm$^{-1}$ i.e. 2962 cm$^{-1}$ (asym), 2869 cm$^{-1}$ (sym) and 2965 cm$^{-1}$, 2867 cm$^{-1}$ (sym) respectively corresponding to the saturated aliphatic C—H methyl group of coordinated dialkyl (methyl/ethyl) dithiocarbamate. The C—H methyl groups have characteristic bending absorptions at 1372 cm$^{-1}$ and 1371 cm$^{-1}$ in complexes (1) and (2) respectively. The C—H bending band(s) associated C—H stretching band(s) with are often determining factor whether methyl groups are present in a molecule. The C—H(—CH$_2$—) methylene coordinated diethyl dithiocarbamate stretching occurs at 2925 cm$^{-1}$ and its corresponding bending appears at 1409 cm$^{-1}$ for complex (2) (D. L. Pavia, G. M. Lampman, S. G. Kriz, Introduction to Spectrochemistry. 3rd Ed., Thomson Learning, USA., (2001) 30-33; R. M. Silverstein, F. X. Webster, *Spectrometric Identification of Organic Compounds*, 6$^{th}$ edition (Wiley, New York, 1998) and T. W. G. Solomons, C. Fryhle *Organic Chemistry*, 7$^{th}$ edition upgrade (Wiley, New York, 2001)—each incorporated herein by reference in its entirety).

The band at 304 cm$^{-1}$ in the far-IR spectrum of complex 0 has been assigned to the v(Au—Cl) vibration, while bands appearing at 282 and 194 cm$^{-1}$ in the far-IR spectra of complexes 1-2 are attributed to the v(Au—S) and v(Au—P) vibrations (K. N. Kouroulis, S. K. Hadjikakou, N. Kourkoumelis, M. Kubicki, L. Male, M. Hursthouse, S. Skoulika, A. K. Metsios, V. Y. Tyurin, A. V. Dolganov, E. R. Milaevag, N. Hadjiliadis, Dalton Trans, (2009) 10446-10456; E. A. Allen, W. Wilkinson, *Spectrochim. Acta*, 2 (1972) 2257-2262; I. S. Butler, A. Neppel, K. R. Plowman, C. F. Shaw, *J. Raman Spectrosc.*, 15 (1984) 310-318; A. G. Jones, D. B. Powell, *Spectrochim. Acta*, 30 (1984) 563-570—each incorporated herein by reference in its entirety).

The $^1$H NMR chemical shifts of complexes (1) and (2) along with their corresponding metal precursor [Au{P(t-Bu)$_3$}(Cl)] and free dialkyl dithiocarbamate ligands are listed in Table 3. A small upfield shift for methyl (—CH$_3$) protons of tert-butyl (t-Bu) hydrogen have been seen for complex (1) compared to free metal precursor chemical shift. A small down field shift for methyl (—CH$_3$) protons of tert-butyl (t-Bu) hydrogen have been observed for complex (2) compared to free metal precursor chemical shift as shown in the Table 3. The slight upfield shifts for proton(s) of the coordinated dimethyl dithiocarbamate and diethyl dithiocarbamate have been seen in gold(I) complexes (1) and (2) respectively in comparison to free dialkyl dithiocarbamate ligands.

The $^{13}$C and $^{31}$P NMR chemical shifts of complexes (1) and (2) along with their corresponding metal precursor [Au{P(t-Bu)$_3$}(Cl)] and free dialkyl dithiocarbamate ligands are presented in Table 4. The $^{13}$C NMR spectra of complexes (1) and (2) showed four and five resonances, respectively, and only the quaternary carbon of the tert-butyl group showed the coupling to phosphorus. Only a small shielding in the chemical shifts for methyl carbons as well as quaternary carbon attached to phosphorus in tri(tert-butyl) phosphine was observed in the complexes compared to that in the A(I) precursor. There are also small upfield chemical shifts of CH$_3$, CH$_2$ and C=S carbons of coordinated dialkyl dithiocarbamate with respect to free dialkyl dithiocarbamate ligands. The $^{13}$C chemical shifts of C=S carbon of dimethylthiocarbamate and diethylthiocarbamate are observed in the range 205-212 ppm. The up field shifts is observed as result of coordinated dialkyl dithiocarbamates in complexes (1) and (2). The P—C coupling constant (J$_{p-c}$) showed a decrease of 3 Hz on complexation.

The molecular structure of complex [Au{P(t-Bu)$_3$}(S$_2$CN(CH$_3$)$_2$)] (1) is shown in FIG. 1. It is a mononuclear ionic complex with one discrete [Au{P(t-Bu)$_3$}(S$_2$CNMe$_2$)] unit containing tri-tertiary butyl phosphine and dimethyl thiocarbamate ligand molecules. Dimethyl thiocarbamate is working as a coordinated counter anion in this complex molecule. The central gold(I) atom is coordinated with one P donor atom of the tri-(t-Bu)$_3$P ligand molecule and S atom of (S$_2$CNMe$_2$)$^-$ anion. The mononuclear Au atom adopts a similar linear P—Au—S coordination geometry like gold (I) complex (2).

X-ray structure contains one asymmetric molecule of complex [Au{P(t-Bu)$_3$}(S$_2$CN(CH$_3$)$_2$)] (1). A linear environment is found around Au atom. The Au1-S1 and Au1-P1 bond distances are 2.3249 (2) and 2.2746 (2) Å respectively. The P1-Au1-S1 bond angle 176.441 (7)°. The bond angle around Au(I) atom show considerable deviation from the ideal linear angle value 180° (Table 6). Table 6 is presented below.

TABLE 6

Selected bond distances (Å) and bond angles (°) for complexes 1 and 2.

| Compound 1 | | Compound 2 | |
|---|---|---|---|
| Bond Length (Å) | | Bond Length (Å) | |
| Au1—P1 | 2.28182 (16) | Au1—P1 | 2.2746 (2) |
| Au1—S1 | 2.32942 (17) | Au1—S1 | 2.3249 (2) |
| Au2—P2 | 2.27538 (17) | S2—C1 | 1.6954 (7) |
| Au2—S3 | 2.31395 (16) | S1—C1 | 1.7452 (9) |
| S2—C1 | 1.6813 (5) | P1—C12 | 1.8885 (11) |

TABLE 6-continued

Selected bond distances (Å) and bond angles (°) for complexes 1 and 2.

| Compound 1 | | Compound 2 | |
|---|---|---|---|
| S1—C1 | 1.7490 (5) | P1—C4 | 1.8971 (8) |
| S4—C18 | 1.6823 (5) | P1—C8 | 1.8989 (9) |
| S3—C18 | 1.7426 (5) | N1—C1 | 1.3294 (10) |
| P1—C6 | 1.8831 (5) | N1—C3 | 1.4601 (12) |
| P1—C14 | 1.9064 (5) | | |
| P1—C10 | 1.9098 (5) | | |
| N1—C1 | 1.3368 (6) | | |
| N1—C2 | 1.4513 (7) | | |
| N1—C4 | 1.5085 (7) | | |
| P1—C6 | 1.8831 (5) | | |
| P1—C14 | 1.9064 (5) | | |
| P1—C10 | 1.9098 (5) | | |
| N1—C1 | 1.3368 (6) | | |
| N1—C2 | 1.4513 (7) | | |
| N1—C4 | 1.5085 (7) | | |
| P1—C6 | 1.8831 (5) | | |
| P2—C23 | 1.8756 (6) | | |
| P2—C27 | 1.8782 (5) | | |
| P2—C31 | 1.9175 (7) | | |
| N2—C18 | 1.3380 (6) | | |
| N2—C21 | 1.4553 (7) | | |
| N2—C19 | 1.4660 (8) | | |
| P2—C23 | 1.8756 (6) | | |
| P2—C27 | 1.8782 (5) | | |
| P2—C31 | 1.9175 (7) | | |
| N2—C18 | 1.3380 (6) | | |
| N2—C21 | 1.4553 (7) | | |
| N2—C19 | 1.4660 (8) | | |
| P2—C23 | 1.8756 (6) | | |

| Bond Angles (°) | | Bond Angles (°) | |
|---|---|---|---|
| P1—Au1—S1 | 172.734 (4) | P1—Au1—S1 | 176.441 (7) |
| C1—S1—Au1 | 101.707 (16) | C1—S1—Au1 | 99.68 (3) |
| P2—Au2—S3 | 170.421 (4) | C12—P1—C4 | 109.73 (4) |
| C18—S3—Au2 | 103.361 (17) | C12—P1—C8 | 109.99 (5) |
| C6—P1—Au1 | 110.049 (16) | C4—P1—C8 | 111.04 (5) |
| C14—P1—Au1 | 108.938 (18) | C12—P1—Au1 | 110.01 (3) |
| C10—P1—Au1 | 107.266 (17) | C4—P1—Au1 | 108.37 (3) |
| C1—N1—C2 | 122.59 (5) | C8—P1—Au1 | 107.67 (3) |
| C1—N1—C4 | 122.28 (4) | S2—C1—S1 | 121.08 (5) |
| C23—P2—Au2 | 107.73 (2) | C1—N1—C2 | 123.85 (7) |
| C27—P2—Au2 | 111.10 (2) | C3—N1—C2 | 113.67 (7) |
| C31—P2—Au2 | 106.95 (2) | N1—C1—S2 | 121.90 (6) |
| C18—N2—C21 | 120.95 (5) | N1—C1—S1 | 117.01 (5) |

The Au—S and Au—P bond distances are 2.337 (1) and 2.243 (1) Å, respectively and are similar to those found in complex (S. Y. Ho, E. R. T. Tiekink, Z. Kristallogr. 220 (2005) 342-344—incorporated herein by reference in its entirety). However, the S—Au—P bond angle is considerably different from those found in [Et$_3$PAu(S$_2$CNEt$_2$)] complex and other mononuclear [(t-Bu)PAu]$^+$ complexes (I. Sanger, H.-W. Lerner, T. Sinke, M. Bolte, Acta Cryst. E68 (2012) m708; P. Lu, T. C. Boorman, A. M. Z. Slawin, I. Larrosa, J. Am. Chem. Soc. 132 (2010) 5580-5581; R. E. Marsh, Acta Cryst. B58 (2002) 893-899; H. Schmidbaur, B. Brachthiuser, O. Steigelmann, H. Beruda, Chem. Ber. 125 (1992) 2705-2710—each incorporated herein by reference in its entirety).

Figure 2:
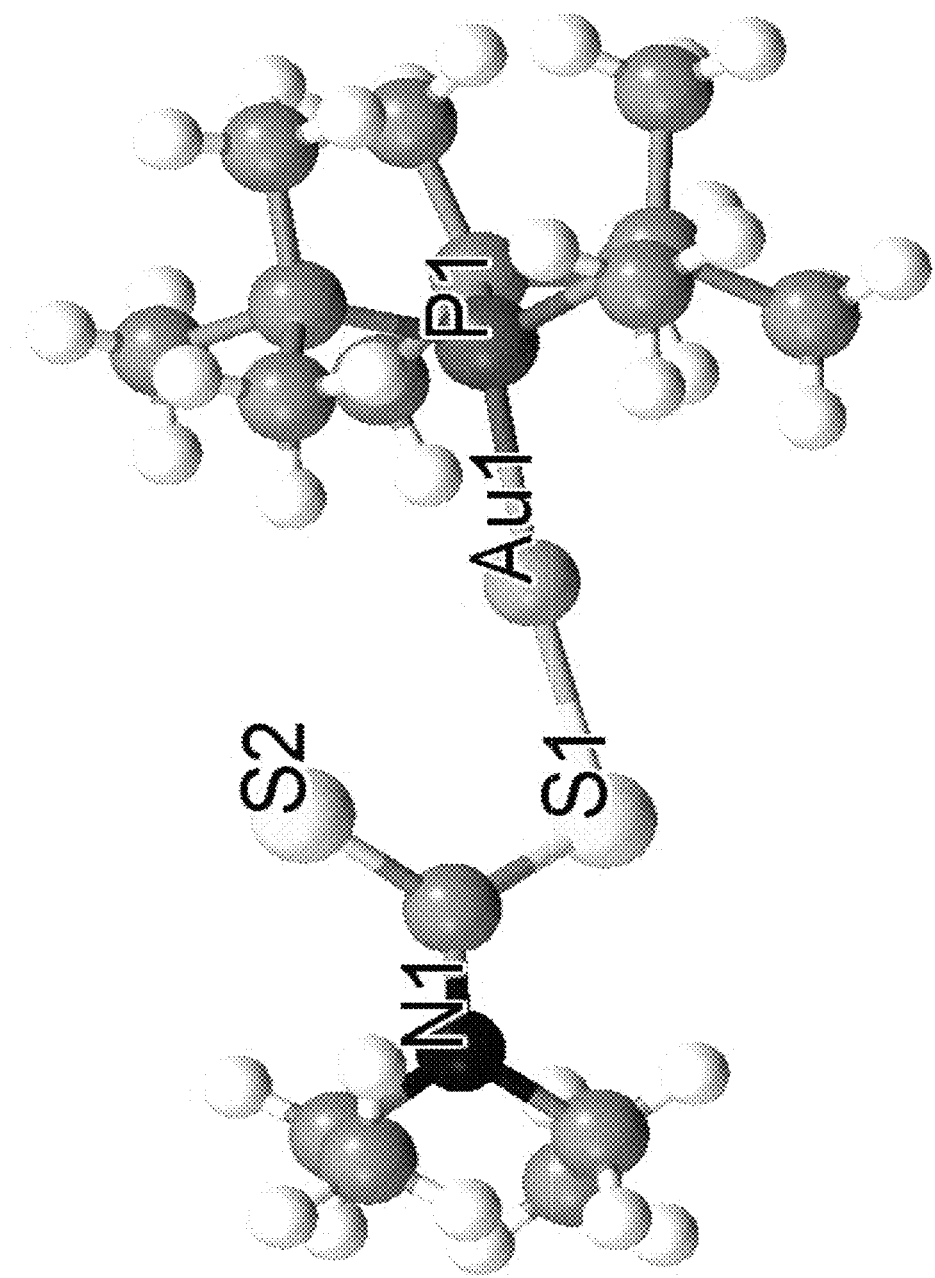
FIG. 2 illustrates molecular structure of mononuclear complex 2.

Molecular structure of [Au{P(t-Bu)$_3$}(S$_2$CN(C$_2$H$_5$)$_2$)] (2) contains two virtually identical molecules of gold(I) complex containing the same (t-Bu)$_3$P ligand molecule and [(S$_2$CNEt$_2$)]$^-$ counter ion as shown in the FIG. 2. In both molecules, gold(I) is coordinated with one P donor atom of (t-Bu)$_3$P ligand molecule and one S donor atom of the [(S$_2$CNEt$_2$)]$^-$ ligand molecule. The Au1-S1 and Au2-53 bond distances are 2.32942 (17) and 2.31395 (16) Å respectively. The Au1-P1 and Au—P2 bond distances are 2.28182 (16) and 2.27538 (17) Å. The Au—S bond distances are very similar to [Au{P(t-Bu)$_3$}(S$_2$CN(CH$_3$)$_2$)] (1) complex and [Et$_3$PAu(S$_2$CNEt$_2$)] complex [51]. The Au—P bond distances are different than [Et$_3$PAu(S$_2$CNEt$_2$)] complex [51] and similar to [Au{P(t-Bu)$_3$}(S$_2$CN(CH$_3$)$_2$)](1) complex.

The geometry around Au1 and Au2 metal atoms is conventionally linear and similar to each other and complex (1). In [Au{P(t-Bu)$_3$}(S$_2$CN(C$_2$H$_5$)$_2$)] molecule 1 and 2, S1-Au1-P1 and S3-Au2-P2 bond angle are 172.734 (4)° and 170.421 (4)° respectively. There is a small distortion from ideal linearity in each molecule as seen in [Au{P(t-Bu)$_3$}(S$_2$CN(CH$_3$)$_2$)] (1) complex and [Et$_3$PAu(S$_2$CNEt$_2$)] complex. These bond angle values around central gold atom in molecule 1 and molecule 2 confirm the presence of pseudo distorted linear geometry around gold(I) atoms in this structure. These bond angle values also show big deviation from ideal linear angle of 180° (Table 6).

The overall geometry of [Au{P(t-Bu)$_3$}(S$_2$CN(C$_2$H$_5$)$_2$)] (2) closely resembles to those Au(I) complexes containing (t-Bu)$_3$P ligand molecule. In this X-ray structure analysis, crystal data shows no aurophilic (Au—Au) attraction.

Figure 3:
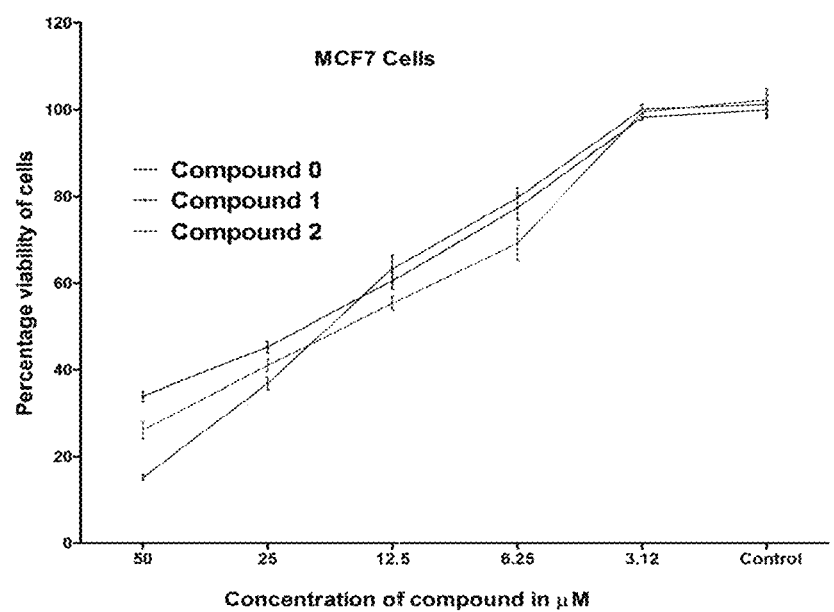
FIG. 3 is a graph illustrating the in vitro cytotoxic effects of a series of concentrations of compound (0) on the MCF7 cell line.
Figure 4:
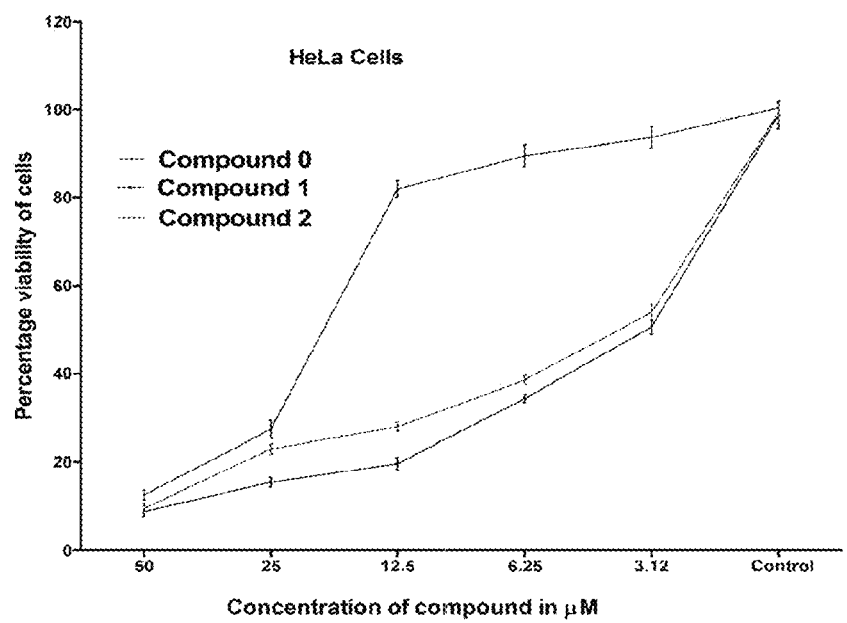
FIG. 4 is a graph illustrating the in vitro cytotoxic effects of a series of concentrations of complex (0) on the HeLa cell line.
Figure 5:
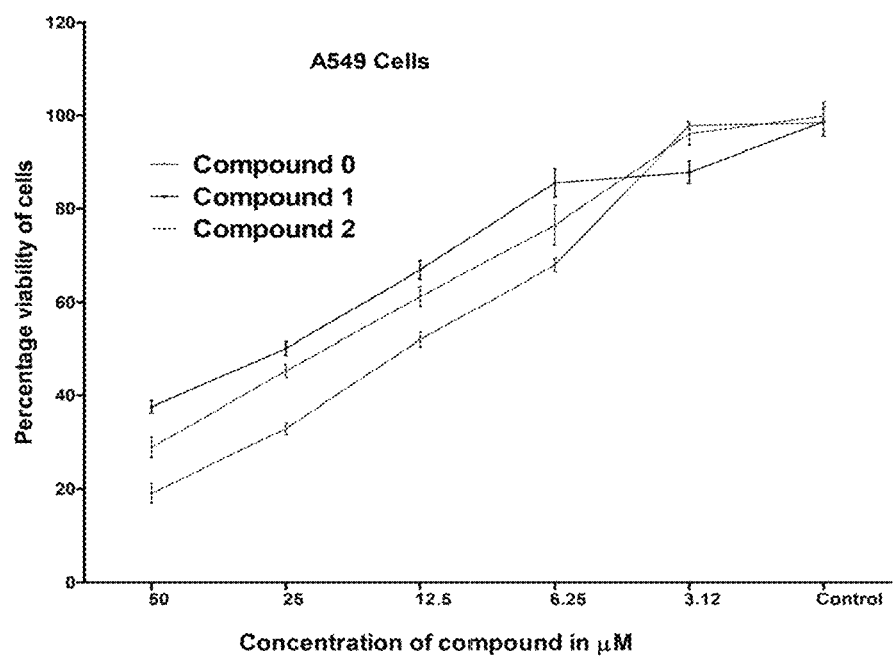
FIG. 5 is a graph illustrating the in vitro cytotoxic effects of a series of concentrations of complex (0) on the A549 cell line.

The in vitro cytotoxicity tests were evaluated for the gold(I) precursor, labeled as (0) and two synthesized complexes labeled as (1) and (2) against three human cancer cell lines, MCF7, HeLa and A549 using MTT assay. The dose dependent cytotoxic effect was obtained by the stipulated increase in concentrations of complexes (0), (1) and (2) against the fixed number of human cancer cells. The IC$_{50}$ concentration of complexes (0), (1) and (2) for different human cell lines are obtained from a curve between complex concentration and percentage viability of cells as shown in FIG. 3, FIG. 4, and FIG. 5. FIG. 3 is a graph of the in vitro cytotoxic effect of series of concentrations of compound (0) on MCF7 cell line. FIG. 4 is a graph of the in vitro cytotoxic effect of series of concentrations of complex (0) on HeLa cell line. FIG. 5 is a graph of the in vitro cytotoxic effect of series of concentrations of complex (0) on A549 cell line. The IC$_{50}$ values of these complexes ranged far and wide between 2.0 to 26.8 µM (Table 7).

Table 7 is presented below.

TABLE 7

IC$_{50}$ Values (µM) of gold(I) complexes against A549, HeLa and MCF7 cancer cell lines.

| Complex | A549 | HeLa | MCF7 |
|---|---|---|---|
| (0) | 14.272 | 16.002 | 16.661 |
| (1) | 26.861 | 2.072 | 21.064 |
| (2) | 19.357 | 3.211 | 16.034 |

Table 8 is presented below.

TABLE 8 in vitro cytotoxic effect of series of concentrations (µM) of gold(I) complexes on percent viability of HeLa (human cervical cancer)

| iM | Complex (0) | Complex (1) | Complex (2) |
|---|---|---|---|
| Control | 100.9 ± 2.9 | 98.7 ± 2.7 | 99.8 ± 2.4 |
| 3.12 | 93.6 ± 2.4 | 50.6 ± 1.5 | 53.9 ± 1.9 |
| 6.25 | 89.5 ± 2.3 | 34.4 ± 0.9 | 38.6 ± 1.2 |
| 12.5 | 81.9 ± 1.9 | 19.5 ± 1.4 | 27.9 ± 1.0 |
| 25 | 27.3 ± 1.5 | 15.3 ± 1.1 | 22.9 ± 1.2 |
| 50 | 12.4 ± 1.1 | 8.7 ± 1.2 | 9.41 ± 1.16 |

The in vitro cytotoxicity of complexes (0), (1) and (2) in terms of IC$_{50}$ values against A549 cell line were found to be 14.272, 26.861 and 19.357 µM respectively. As far as in vitro cytotoxicity against A549 cell line is concerned, the precursor complex (0) with IC$_{50}$ value i.e. 14.272 is better than complexes (1) and (2). However, complex (1) is a better cytotoxic agent than complex (2) against A549 cell line.

The in vitro cytotoxicity of complexes (0), (1) and (2) in terms of IC$_{50}$ values against HeLa cell line were found to be 16.002, 2.072 and 3.211 respectively. The complex (1) and complex (2) with IC$_{50}$ values i.e. 2.072 and 3.211 are far much better cytotoxic candidates than precursor complex (0). Both complexes (1) and (2) have similar in vitro cytotoxicity against HeLa cell line. Complex (1) is a better cytotoxic agent in vis-a-vis to complex (2).

The in vitro cytotoxicity of complexes (0), (1) and (2) in terms of IC$_{50}$ values against MCF7 cell line are 16.661, 21.064 and 16.034 µM respectively. The precursor (0) and complex (2) with IC$_{50}$ values i.e. 16.661 and 16.034 are noticeably much better than complex (1). Both precursor (0) and (2) have similar in vitro cytotoxicity against MCF7 cell line. However, precursor (0) is marginally better cytotoxic agent in evaluation to complex (2).

Among all three cell lines, complexes (1) and (2) were found to be most effective against HeLa cell line with IC$_{50}$ concentration of 2.072 and 3.211 µM respectively. Complex (2) shows better in vitro cytotoxicity than complex (1) against A549 and MCF7 cell lines. But in case of HeLa cell line, complex (1) indicates better in vitro cytotoxicity than complex (2). Complex (0) showed almost similar results with all the human cell lines with IC$_{50}$ i.e. 16.661, 16.002 and 14.272 µM for MCF7, HeLa and A549, cancer cell lines respectively.

The in vitro cytotoxic activity of the compounds against HeLa cell line (human cervical cancer) are promising in comparison to other MCF7 (human breast cancer) and A549 (human lung carcinoma) cell lines respectively. These compounds are less active against MCF7 (human breast cancer) and A549 (human lung carcinoma) cell lines comparative to the metal precursor gold(I) complex (0). The cytotoxic effects of compounds (1) and (2) of 50 µg/mL (Table 7) concentration on HeLa cell line (human cervical cancer) better than Auranofin gold(I) compound The cytotoxic effects of [Au(P(t-Bu)$_3$)(S$_2$CN(CH$_3$)$_2$)] (1), and [Au(P(t-Bu)$_3$)(S$_2$CN(C$_2$H$_5$)$_2$)] (2) complexes against human cervical cancer (HeLa) cell line are promising. The overall anticancer activities of both complexes against all three human cancer cell lines are at the µg/mL level and particularly against HeLa cell line; MIC values are between 0.21-0.23 µg/mL. In vivo cytotoxic valuation is recommended for these new gold(I) complexes.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A method for treating cancer or a tumor comprising administering, in a cytotoxically effective amount, a gold complex of formula:

$$Au\{P(t\text{-}Bu)_3\}(S_2CN(R)_2)$$

where R is CH$_3$ or C$_2$H$_5$,
to a subject in need of treatment for a human cervical cancer,
wherein the gold complex is administered in the form of a solution.

2. The method of claim 1, wherein the gold complex is administered in the form of a solution in the presence of fetal bovine serum.

* * * * *